United States Patent [19]

Tatlow et al.

[11] Patent Number: 4,562,183

[45] Date of Patent: Dec. 31, 1985

[54] PERFLUORO-1-AZABICYCLO(5,3,0)DEC-ANE COMPOUNDS USEFUL AS BLOOD SUBSTITUTES

[75] Inventors: John C. Tatlow; Raymond G. Plevey, both of Birmingham; David E. M. Wotton, Bristol; Colin R. Sargent, Clevedon, all of England

[73] Assignee: I.S.C. Chemicals Limited, London, England

[21] Appl. No.: 460,393

[22] Filed: Jan. 24, 1983

[30] Foreign Application Priority Data

Jan. 22, 1982 [GB] United Kingdom ................. 8201821

[51] Int. Cl.[4] .................... C07D 499/00; A61K 31/40
[52] U.S. Cl. .................................... 514/214; 514/832; 514/833; 260/245.7
[58] Field of Search ................... 260/245.7; 514/214, 514/832, 833

[56] References Cited

U.S. PATENT DOCUMENTS

| | | | |
|---|---|---|---|
| 3,674,785 | 7/1972 | Mitsch | 544/56 |
| 4,186,253 | 1/1980 | Yokoyama et al. | 424/352 |
| 4,425,347 | 1/1984 | Yokoyama et al. | 514/832 X |
| 4,526,969 | 7/1985 | Yokoyama et al. | 260/245.7 X |

OTHER PUBLICATIONS

Plevey et al., *Journal of Fluorine Chemistry, 21 (1982) pp. 413–428, CA 197016, vol. 98 (1983).*

Primary Examiner—Donald G. Daus
Assistant Examiner—William A. Teoli, Jr.
Attorney, Agent, or Firm—Holman & Stern

[57] ABSTRACT

Novel perfluorinated heterocyclic compounds have an azabicyclodecane structure with fused 5- and 7-membered rings incorporating a bridgehead nitrogen atom. They are prepared by cobalt (III) fluoride fluorination of quinolines or alkyl quinolines and are useful, when emulsified in aqueous media, as blood substitutes or organ perfusates, prior to transplant.

4 Claims, No Drawings

PERFLUORO-1-AZABICYCLO(5,3,0)DECANE COMPOUNDS USEFUL AS BLOOD SUBSTITUTES

This invention relates to novel perfluorinated heterocyclic compounds and emulsions containing them.

There is a need for a functional liquid to serve as a blood substitute and as a perfusate for organ preservation prior to transplant. Such a liquid should have adequate oxygen-carrying capacity and the ability to emulsify in aqueous media but should not be hydrolysed or otherwise degraded in body tissues.

Compounds used in a commercial blood substitute, Fluosol DA (R.T.M.), are perfluorodecalin (which does not easily give a stable emulsion in aqueous media) and perfluorotripropylamine (which gives a more stable emulsion than perfluorodecalin, but which has a longer retention time in the body).

This invention, in the first aspect, consists in novel perfluoroheterocyclic compounds perfluoroazabicyclodecane, $C_9F_{17}N$ of boiling point 127°–129° C. and its lower (1–2 C-atom) homologues.

It is believed that these new compounds have a 7-membered ring fused with a 5-membered ring in their structure, as shown below:

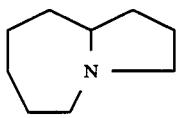

The nitrogen atom in the new compounds is connected to 3-carbon atoms i.e. it is in a bridgehead position. The preferred homologue is a compound with a trifluoromethyl group in the α-position i.e. attached to a carbon atom adjacent to the N-atom.

In a second aspect the invention consists in a method of producing perfluoro-azabicyclodecane and its lower (1–2 C-atom) homologues which method comprises reacting quinoline or an alkyl quinoline with a higher-valent metal fluoride at 250°–400° C. in an inert reactor to produce a fully-fluorinated product. During fluorination a shift of bonds takes place so that the nitrogen atom in the product is in a tertiary position giving a principal product with 5- and 7-membered rings fused together.

By a "higher valent metal fluoride" we mean a metal fluoride in a higher valency state such as cobalt (III) fluoride $CoF_3$ or $CsCoF_4$ which is reduced to a lower valency state while acting as a fluorinating agent.

The product may be purified by fractional distillation and perfluoro-1-azabicyclo(5,3,0)decane has the following physical properties:

Boiling range 127°–129° C.
Refractive index at 22° C. $n_D^{22} = 1.3100$
Specific gravity at 20° C. = 1.900
Pour point = −41° to −42° C.
Solubilities at 25° C.

| Solvent | Solubility of perfluoro-1-azabicyclo(5,3,0)decane in 100 g solvent |
| --- | --- |
| Water | hardly soluble |
| Hexane | miscible |
| Trichloro-trifluoro-ethane | miscible |
| Acetone | 6.84 g |

| Solvent | Solubility of perfluoro-1-azabicyclo(5,3,0)decane in 100 g solvent |
| --- | --- |
| Methanol | 1.36 g |

In a third aspect the invention consists in an oil-in-water emulsion comprising perfluoro-azabicyclodecane or a lower (1–2 C) homologue dispersed in an aqueous medium by means of a surface active agent. Preferably the surface active agent is non-ionic.

The invention will be further illustrated by the following Examples of the preparation of novel perfluoro-heterocyclic compounds in accordance with the invention.

EXAMPLE 1

In a typical experiment, quinoline (150 g) was passed over cobalt (III) fluoride (10 kg) in a paddle-stirred horizontal nickel reactor at 350° (following the procedure in Advances in Fluorine Chemistry Vol. 1 p. 166) to give a crude liquid fluorocarbon (335 g) which was washed thoroughly with water and dried over calcium oxide. Fractional distillation of combined product from several fluorinations (in a 4 ft glass column with nickel Dixon gauzes) gave perfluoro-1-azabicyclo(5,3,0)decane, $C_9F_{17}N$, as a colourless liquid b.p. 127°–129° (24.5% by wt. of the crude product). Neighbouring fractions contain some $C_9F_{17}N$ mixed with other compounds.

EXAMPLE 2

2-Methyl quinoline was fluorinated over cobalt (III) fluoride at 320°–330° C., following the procedure described in Example 1. The product was a clear colourless liquid (typically 212 g of product from 100 g of input). Product from several fluorination runs was combined, washed and dried over CaO and $MgSO_4$. The mixture was fractionally distilled (3 ft glass column with nickel Dixon gauzes). Fractional distillation gave a compound (b.p. 146°–148° C.) for which $^{19}F$ n.m.r. indicates the absence of N—$CF_3$ groups and the presence of a C—$CF_3$ group, which is consistent with a —$CF_3$ group attached to a carbon atom adjacent to the bridgehead nitrogent atom. No N—F bonds were detected (from n.m.r.) and from its infra red spectrum the compound is clearly saturated. The relative molecular mass (by mass spectrometry) was 495 ($C_{10}F_{19}N$). The product is base-stable and its structure is consistent with perfluoro-1-aza-2-methyl(5,3,0)decane.

The utility of the compounds according to the invention as a blood-substitute or a perfusate for organ preservation will be illustrated as follows.

Potential use as an oxygen carrier for medical applications in comparison with perfluorodecalin (see for example U.S. Pat. No. 4,186,253).

1. EMULSION FORMING CAPACITY

To 10 ml. of perfluoro-1-azabicyclo(5,3,0)decane (ABCD) was added 10 ml. of solution made by dissolving 8.0 g of a non-ionic, polyoxyethylene-polyoxypropylene surfactant ('Pluronic F68', RTM) in 220 ml. of deionised water. The mixture was emulsified for a few minutes using a high speed mixer to form an emulsion having the appearance of diluted milk. On standing at room temperature overnight, there was a minor amount of separation ('creaming') of the emulsion.

In a comparison test, an emulsion was formed using perfluorodecalin. An emulsion of similar appearance to that formed with ABCD required about 10 minutes emulsification. On standing over-night pronounced creaming occurred.

2. OXYGEN SOLUBILITY

A portion of 20 ml. of ABCD was degassed by boiling and cooled to 20° C. while being bubbled with oxygen gas. The oxygen-saturated liquid was then degassed under vacuum and the gas evolved was collected and its volume measured at a known temperature and pressure. After allowing for the vapour pressure of the fluorocarbon, the solubility of oxygen was calculated to be in the range $45 \pm 10$ mls of $O_2$ (at 760 mm Hg & 0° C.) per 100 ml. of fluorocarbon. The solubility of oxygen in ABCD is thus adequate to permit the use of this fluorocarbon as an oxygen carrier for medical use.

3. USE OF PERFLUORO-AZABICYCLODECANE EMULSIONS AS BLOOD-SUBSTITUTES

ABCD was evaluated as candidate for an artificial blood substitute from the aspects of toxicity, feasibility of emulsification and excretion rate from the organs.

Toxicity

Wistar strain male rats administered with ABCD emulsion (dose as ABCD: 4 g/kg) gained weight favourably.

Stability of emulsion

In order to evaluate the feasibility of emulsification, ABCD was emulsified with yolk phospholipids by using a Manton-Gaulin homogenizer and the stability to heating at 100° C. for 30 minutes and storage at 4° C. and 25° C. for 2 weeks were examined. The emulsion was acceptably stable over these periods.

Excretion rate

ABCD was very rapidly eliminated from the organs. 2 weeks after injection only trace amounts of ABCD were detected in all organs.

4. RETENTION OF PERFLUORO-1-AZABICYCLO(5,3,0)DECANE BODY ORGANS WITH TIME

Gas chromatography results—rats injected with emulsion of ABCD (0.32 ml. fluorocarbon per 100 gm body weight). The following residual fluorocarbon concentrations were observed. (In mg. fluorocarbon/gm tissue).

|  | 5 Days | 7 Days (Av. of 2) | 10 Days | 14 Days (Av. of 2 except *) | 21 Days |
|---|---|---|---|---|---|
| Spleen | 43.48 | 22.30 | 120.42 | 3.69* | 1.12 |
| Kidney | 0.17 | 0.10 | 0.19 | 0.15 | 0.16 |
| Liver | 11.81 | 6.73 | 2.51 | 0.38 | 0.04 |
| Lung | 0.56 | 0.10 | 0.16 | 0.15 | 0.15 |
| Heart | 0.13 | 0.45 | 0.26 | 0.18 | 0.16 |

We claim:
1. A perfluoroazabicyclodecane compound having a bridgehead nitrogen in its structure wherein said compound is selected from the group consisting of perfluoro-1-azabicyclo(5,3,0)decane, which has fused 5- and 7-membered rings, and its perfluoroalkyl homologues of 1–2 carbon atoms.

2. A compound according to claim 1, which has a trifluoromethyl group attached to a carbon atom adjacent to a bridgehead nitrogen atom of its structure.

3. An oil-in-water emulsion useful as a blood substitute comprising a perfluoroazabicyclodecane compound having a bridgehead nitrogen in its structure when said compound is dispersed in an aqueous phase by a surface active agent wherein said compound is selected from the group consisting of perfluoro-1-azabicyclo(5,3,0)decane, which has fused 5- and 7-membered rings, and its perfluoro alkyl homologues of 1–2 carbon atoms.

4. The emulsion according to claim 3, in which the surface active agent is non-ionic in character.

* * * * *